(12) United States Patent
Zuckerman-Stark et al.

(10) Patent No.: US 11,771,369 B2
(45) Date of Patent: *Oct. 3, 2023

(54) DEVICE AND METHOD FOR DETERMINING SPINAL CORD STIMULATION EFFICACY

(71) Applicant: Medasense Biometrics, Ltd., Ramat Gan (IL)

(72) Inventors: Galit Zuckerman-Stark, Tel Aviv (IL); Noam Racheli, Olesh (IL); Nir Ben-Israel, Tel Aviv (IL)

(73) Assignee: MEDASENSE BIOMETRICS LTD., Ramat Gan (IL)

( * ) Notice: Subject to any disclaimer, the term of this patent is extended or adjusted under 35 U.S.C. 154(b) by 19 days.

This patent is subject to a terminal disclaimer.

(21) Appl. No.: 17/328,617

(22) Filed: May 24, 2021

(65) Prior Publication Data

US 2021/0275093 A1    Sep. 9, 2021

Related U.S. Application Data

(63) Continuation of application No. 16/255,221, filed on Jan. 23, 2019, now Pat. No. 11,020,052, which is a
(Continued)

(51) Int. Cl.
*A61B 5/00* (2006.01)
*A61N 1/36* (2006.01)
(Continued)

(52) U.S. Cl.
CPC .......... *A61B 5/4848* (2013.01); *A61B 5/4824* (2013.01); *A61B 5/4836* (2013.01);
(Continued)

(58) Field of Classification Search
CPC ... A61B 5/4848; A61B 5/4824; A61B 5/4836; A61B 5/7264; A61B 5/02416;
(Continued)

(56) References Cited

U.S. PATENT DOCUMENTS

| 6,659,968 B1 | 12/2003 | McClure |
| 6,871,099 B1 | 3/2005 | Whitehurst |

(Continued)

FOREIGN PATENT DOCUMENTS

| WO | 2009129486 | 10/2009 |
| WO | 2010134068 | 11/2010 |

(Continued)

OTHER PUBLICATIONS

Bruhn et al., (2000) Approximate entropy as an electroencephalographic measure of anesthetic drug effect during desflurane anesthesia. Anesthesiology 92(3):715-26.
(Continued)

*Primary Examiner* — Paula J Stice
(74) *Attorney, Agent, or Firm* — Greenberg Traurig, LLP

(57) ABSTRACT

Device and method for determining an efficacy of chronic pain treatment including providing a first set of at least one stimulus to a subject, obtaining first measurements of at least two physiological parameters in response to the first set of at least one stimulus, providing chronic pain treatment to the subject, providing a second set of at least one stimulus to the subject, obtaining second measurements of the at least two physiological parameters in response to the second set of at least one stimulus; and determining an efficacy of the chronic pain treatment by applying a classification algorithm on the first and second measurements of the at least two physiological parameters.

10 Claims, 5 Drawing Sheets

Related U.S. Application Data continuation of application No. 15/025,284, filed as application No. PCT/IL2014/050851 on Sep. 29, 2014, now Pat. No. 10,231,666.

(60) Provisional application No. 61/884,089, filed on Sep. 29, 2013.

(51) Int. Cl.

| | | |
|---|---|---|
| *A61N 1/372* | (2006.01) | |
| *A61B 5/0205* | (2006.01) | |
| *A61B 5/021* | (2006.01) | |
| *A61B 5/0533* | (2021.01) | |
| *A61B 5/08* | (2006.01) | |
| *A61B 5/083* | (2006.01) | |
| *A61B 5/024* | (2006.01) | |
| *A61B 5/318* | (2021.01) | |
| *A61B 5/369* | (2021.01) | |
| *A61B 5/389* | (2021.01) | |
| *A61B 5/398* | (2021.01) | |
| *A61B 5/145* | (2006.01) | |

(52) U.S. Cl.
CPC ........ *A61B 5/7264* (2013.01); *A61N 1/36071* (2013.01); *A61N 1/36135* (2013.01); *A61N 1/36139* (2013.01); *A61N 1/37241* (2013.01); *A61B 5/0075* (2013.01); *A61B 5/021* (2013.01); *A61B 5/02055* (2013.01); *A61B 5/02416* (2013.01); *A61B 5/0533* (2013.01); *A61B 5/08* (2013.01); *A61B 5/0816* (2013.01); *A61B 5/0836* (2013.01); *A61B 5/14542* (2013.01); *A61B 5/318* (2021.01); *A61B 5/369* (2021.01); *A61B 5/389* (2021.01); *A61B 5/398* (2021.01); *A61N 1/37247* (2013.01)

(58) Field of Classification Search
CPC .. A61B 5/0533; A61B 5/318; A61N 1/36071; A61N 1/36135; A61N 1/36139; A61N 1/37241

See application file for complete search history.

(56) References Cited

U.S. PATENT DOCUMENTS

| | | | |
|---|---|---|---|
| 7,407,485 | B2 | 8/2008 | Huiku |
| 7,463,927 | B1 | 12/2008 | Chaouat |
| 7,801,601 | B2 | 9/2010 | Maschino |
| 7,801,619 | B2 | 9/2010 | Gerber |
| 2003/0032992 | A1 | 2/2003 | Thacker |
| 2005/0075669 | A1 | 4/2005 | King |
| 2005/0209513 | A1 | 9/2005 | Heruth |
| 2006/0195159 | A1 | 8/2006 | Bradley |
| 2006/0270944 | A1 | 11/2006 | King |
| 2007/0255118 | A1 | 11/2007 | Miesel |
| 2008/0269812 | A1 | 10/2008 | Gerber |
| 2009/0157141 | A1 | 6/2009 | Chiao |
| 2010/0010585 | A1 | 1/2010 | Davis |
| 2010/0114237 | A1 | 5/2010 | Giftakis |
| 2011/0119212 | A1 | 5/2011 | De Bruin |
| 2011/0295335 | A1 | 12/2011 | Sharma |
| 2014/0275827 | A1 | 9/2014 | Gill |

FOREIGN PATENT DOCUMENTS

| | | |
|---|---|---|
| WO | 2012151449 | 11/2012 |
| WO | 2013162706 | 10/2013 |

OTHER PUBLICATIONS

Goncharova and Barlow (1990) Changes in EEG mean frequency and spectral purity during spontaneous alpha blocking. Electroencephalogr Clin Neurophysiol 76(3):197-204.

Gridley and van den Dolder (2001) The percentage improvement in Pain Scale as a measure of physiotherapy treatment effects. Aust J Physiother 47(2):133-8.

Gullman et al., (2009) Spinal cord stimulation as a novel approach to the treatment of refractory neuropathic mediastinal pain. Pain Pract 9(4):308-11.

Hjorth (1973) The physical significance of time domain descriptors in EEG analysis. Electroencephalogr Clin Neurophysiol 34(3):321-5.

Klomp et al., (2009) What is the evidence on efficacy of spinal cord stimulation in (subgroups of) patients with critical imb ischemia? Ann Vasc Surg 23(3):355-63.

Lazaro et al., (2001) Psychometric properties of a Spanish version of the McGill Pain Questionnaire in several Spanish-speaking countries. Clin J Pain 17(4):365-74.

Pop-Jordanova and Pop-Jordanov (2005) Psectrum-weighted EEG frequency ("brain-rate") as a quantitative indicator of mental arousal. Prilozi 26(2):35-42.

Schlogl an Supp (2006) Analyzing event-related EEG data with multivariate autoregressive parameters. Prog Brain Res 159:135-47.

Shealy et al., (1967) Electrical inhibition of pain by stimulation of the dorsal columns: preliminary clinical report. Anesth Analg 46(4):489-91.

Thomas and Evans (1989) Lower oesophageal contractility monitoring during anesthesia for cardiac surgery: preliminary observations. Ann R Coll Surg Engl 71(5):311-5.

Wackermann (1999) Towards a quantitative characterisation of functional states of the brain: from the non-linear methodology to the global linear description. Int J Psychophysiol 34(1):65-80.

Weiss et al., (1980) Pulse transit time in the analysis of autonomic nervous system effects on the cardiovascular system. Psychophysiology 17(2):202-7.

DEVICE AND METHOD FOR DETERMINING SPINAL CORD STIMULATION EFFICACY

RELATED APPLICATION DATA

This application is a continuation of U.S. Utility patent application Ser. No. 16/255,221, filed Jan. 23, 2019, now U.S. Pat. No. 11,020,052, issued on Jun. 1, 2021, which is a continuation of U.S. Utility patent application Ser. No. 15/025,284, filed Mar. 28, 2016, now U.S. Pat. No. 10,231,666, issued on Mar. 19, 2019, which is the U.S. National Stage Entry of International Application No. PCT/IL2014/050851, filed Sep. 29, 2014, which claims the benefit of U.S. Provisional Patent Application No. 61/884,089, filed Sep. 29, 2013. Each of the foregoing applications are hereby incorporated by reference in their entirety for all purposes.

TECHNICAL FIELD

The present disclosure relates generally to the field of medical devices and, more particularly, electrical nerve stimulators.

BACKGROUND

Spinal cord stimulation (SCS) is a widely used treatment for a number of pain conditions and is frequently considered a suitable pain management option when conservative or less invasive techniques have proven to be ineffective.

Spinal Cord Stimulation (SCS), as its name suggests, provides nerve stimulation to the spinal cord by introducing electrical pulses in the dorsal aspect of the spinal cord. This form of stimulation is believed to interfere with the transmission of pain signals to the brain and to replace them with a more pleasant sensation called paresthesia. Spinal cord stimulation (SCS), in the simplest form, consists of stimulating electrodes, implanted in the epidural space, an electrical pulse generator, implanted in the lower abdominal area or gluteal region, conducting wires connecting the electrodes to the generator, and a remote control of the generator.

While research on SCS is in its infancy, it is clear that there is a substantial variation in the degree of benefit of SCS between patients. To date before proceeding with permanent SCS implantation, a stimulation trial is performed. The SCS trial procedure is a minimally invasive procedure (similar to placing an epidural catheter). The trial allows the patients to evaluate the SCS analgesic activity in their everyday surroundings. The trial can last for between hours and up to a week, whereafter efficacy is subjectively determined based on patient's sense of pain relief. The criteria for a successful trial is at least a 50% reduction in pain, a decrease in analgesic intake and significant functional improvement. Most patients who are not sure that the spinal cord stimulator trial helped will not get a permanent spinal cord stimulator.

Despite the strict criteria as many as 20-30% of patients fail to experience pain relief following permanent SCS implantation. Oppositely, patients who fail to acknowledge a real reduction in pain relief may not get a permanent SCS implantation, even though they could have benefit therefrom.

SUMMARY

Aspects of the disclosure, in some embodiments thereof, relate to device and method for assessing chronic pain treatment efficacy. The method disclosed herein may include providing a first set of stimuli to a subject; obtaining first measurements of at least two physiological parameters in response to the first set of stimuli; providing a chronic pain treatment to the subject; providing a second set of stimuli to the subject; obtaining second measurements of the at least two physiological parameters in response to the second set of stimuli; and determining an efficacy of the chronic pain treatment by applying a classification algorithm on the first and second measurements of the at least two physiological parameters, obtained in response to the first and second set of stimuli, respectively.

Subjects suffering from chronic pain do so during a prolonged period of time, consequently affecting brain structure and function. As a result, recognizing pain relief in response to short term treatments may be difficult for a subject suffering from chronic pain. The difficulty of assessing pain relief for patients suffering from chronic pain is further augmented by the fact that psychological factors may affect the assessment. The psychological factors may, on the one hand, be factors leading to exaggeration of real efficacy, for example due to keenness of pain relief; and on the other hand, be factors leading to understatement of real efficacy, for example due to fear of surgery, such as implantation of a permanent SCS device. In effect, as many as 20-30% of patients fail to experience pain relief following permanent SCS implantation, despite pledging pain relief during a SCS trial, and oppositely real benefiters may be overseen due to a failure to recognize the benefit of the SCS trial.

Advantageously, the device and method, disclosed herein, may enable objective assessment of chronic pain treatment efficacy in a subject. The method may be of particular benefit when assessing the efficacy of a chronic pain treatment trials, such as implantation of a temporary SCS device prior to permanent SCS implantation.

Similarly, desensitization and/or resistance to the chronic pain treatment may be developed during time. As desensitization and/or resistance may develop gradually it may initially go unrecognized by the patient until a certain pain threshold is reached, thereby causing a setback in the treatment of the chronic pain.

Advantageously, the device and method disclosed herein, enable periodical assessment of the efficacy of a chronic pain treatment in a subject, thereby identifying changes in efficacy which may require adjustments and/or changes in treatment regimen and/or type; this preferably prior to reversion of pain and treatment setback. Such assessment may be of particular importance prior to surgical procedures, such as the procedure required for changing batteries in a permanently implanted SCS device.

The level of pain experienced by the subject suffering from chronic pain may be variable depending on factors such as activity level (whether current activity or aftermaths of a prior activity), body positioning, weather or the like. Advantageously, the device and method, disclosed herein, enables adjustment of SCS operating parameters based on measurements of at least one physiological signal, until SCS parameters yielding a highest efficacy are identified. The changes in the SCS parameters are thus based on an objective assessment of SCS efficacy, rather than on changes in the activity of the subject per se, as known in the art.

According to some embodiments, there is provided a method for determining an efficacy of spinal cord stimulation (SCS) treatment in a subject with chronic pain, the method comprising: providing a first set of at least one stimulus to the subject; obtaining first measurements of at least two physiological parameters in response to the first set of at least one stimulus; providing SCS treatment to the subject; providing a second set of at least one stimulus to the subject; obtaining second measurements of the at least two physiological parameters in response to the second set of at least one stimulus and the SCS treatment; and determining an efficacy of the SCS treatment by applying a classification algorithm on the first and second measurements of the at least two physiological parameters, obtained in response to the first and second set of at least one stimulus, respectively.

According to some embodiments, applying the classification algorithm comprises directly or indirectly comparing the first and second measurements to pre-stored data sets of measurements obtained from subjects with known SCS treatment efficacies.

According to some embodiments, determining the efficacy of the SCS treatment is further based on patient demographic data.

According to some embodiments, providing the SCS treatment comprises providing a trial SCS treatment. According to some embodiments, the trial SCS treatment comprises implanting into the subject a temporary spinal cord stimulator comprising stimulating electrodes only. According to some embodiments, the trial SCS treatment comprises implanting into the subject a temporary spinal cord stimulator without implanting an electrical pulse generator.

According to some embodiments, the method further comprises predicting a treatment efficacy of long-term SCS treatment based on the determined efficacy of the trial SCS treatment.

According to some embodiments, the method further comprises providing a treatment recommendation based on the predicted treatment efficacy.

According to some embodiments, the at least one stimulus is selected from: painful stimulus on non-painful area, painful stimulus on painful area, non-painful stimulus on non-painful area, non-painful stimulus on painful area. According to some embodiments, the source of the at least one stimulus is selected from tetanic stimulus, thermal (heat or cold) stimulus, pressure stimulus, touch (tickle, itch, crude, flutter, pressure) stimulus, electric stimulus, mechanical stimulus, proprioception stimulus, chemical stimulus or combinations thereof. According to some embodiments, the painful stimulus and the non-painful stimulus is of a different or a same source.

According to some embodiments, the at least two physiological parameters are selected from the group consisting of photoplethysmograph (PPG) Peak (P) amplitude, mean PPG Peak (P) amplitude, standard deviation (std) of PPG Peak (P) amplitude, Trough (T) amplitude, mean Trough (T) amplitude, std of Trough (T) amplitude; PPG dicrotic notch (N) amplitude, mean dicrotic notch (N) amplitude, std of dicrotic notch (N) amplitude, PPG peak to peak time intervals, PPG peak to peak interval mean, PPG peak to peak interval std; power spectrum of the PPG peak to peak intervals: VLF Power, LF Power and HF Power; PPG envelope-time analysis; PPG envelope spectral analysis; galvanic skin response (GSR) amplitude, GSR mean amplitude, GSR amplitude std; GSR Peak (P) amplitude, mean Peak (P) amplitude and Peak (P) amplitude std; GSR peak to peak time intervals, mean GSR peak to peak time interval; GSR peak to peak time intervals std; Phasic EDA: amplitude, mean amplitude and std of amplitude, Temperature amplitude, mean amplitude and std of amplitude; Temp Peak (P) amplitude, mean amplitude and std of amplitude; Temperature peak to peak time intervals, mean and std (variability) of interval; PPG to PPG Pulse transit time, ECG to PPG Pulse Transition time; ECG R to R time intervals, mean and std (variability) of intervals; Power of VLF, LF and HF frequency bands of power spectrum of the ECG R to R intervals (heart rate variability); Upper peak amplitude, mean amplitude and STD of amplitude; Respiratory rate, mean rate and std rate; Power of the frequency bands of power spectrum of EMG signal; EMG Power Spectrum Mean frequency; EMG Power Spectrum Highest Peak Frequency; Power of the alpha, beta, gamma, delta, theta frequency bands of power spectrum of EEG/FEMG signal; EMG Power Spectrum Mean frequency; EMG Power Spectral edge frequency; Coherence between 2 or more EEG/FEMG channels; frequency of movement, axis of movement and any combination thereof.

According to some embodiments, the at least two physiological parameters are selected from the group consisting of PPG amplitude, PPG amplitude variation, pulse rate, pulse rate variability, GSR level, GSR fluctuations or any combination thereof.

According to some embodiments, the at least two physiological parameters are derived from at least one physiological signal selected from photoplethysmograph (PPG), galvanic skin response (GSR), electrocardiogram (ECG), blood pressure, respiration, internal body temperature, skin temperature, electrooculography (EOG), pupil diameter, electroencephalogram (EEG), frontalis electromyogram (FEMG), electromyography (EMG), electro-gastro-gram (EGG), laser Doppler velocimetry (LDV), dynamic light scattering (DLS), Near Infrared Spectroscopy (NIRS), partial pressure of carbon dioxide, and accelerometer readings.

According to some embodiments, the at least two physiological parameters are derived from a photoplethysmograph (PPG) signal and a galvanic skin response signal.

According to some embodiments, the method further comprises obtaining at least three physiological parameters.

According to some embodiments, the chronic pain is selected from Failed Back Surgery Syndrome (FBSS), complex regional pain syndrome (CRPS), Radiculopathy, Peripheral Vascular Disease (PVD), Neuralgia, Neuropathic pain, refractory angina pectoris (RAP), Ischemic pain. According to some embodiments, there is provided a method for calibrating spinal cord stimulation (SCS) treatment in a subject, the method comprising: providing a SCS treatment being characterized by at least one SCS parameter; varying a value of one of the at least one SCS parameter along a dynamic range thereof; obtaining measurements of at least two physiological parameters in response to varying the value of the one SCS parameter along the dynamic range thereof; determining an efficacy of the SCS treatment along the dynamic range of the varied SCS parameter by applying a classification algorithm to the at least two physiological parameters obtained in response to varying the one SCS parameter along the dynamic range thereof; and selecting the value of the one SCS parameter yielding the highest efficacy.

According to some embodiments, the remaining parameters of the at least one parameters are fixed while varying the one parameter.

According to some embodiments, the at least one SCS parameter comprises type of stimulation, stimulation frequency, duration, pulse width, intensity, waveform, wave pattern, signal, amplitude, onset timing, delay, treatment length, treatment period, onset delay or any combination thereof.

According to some embodiments, varying the SCS parameter along the dynamic range comprises making continuous, incremental and/or step wise changes in the value of the SCS parameter.

According to some embodiments, there is provided a system for determining efficacy of a SCS treatment, the system comprising a processor configured to obtain a first measurements of at least two physiological parameters in response to a first set of at least one stimulus; obtain a second measurements of the at least two physiological parameters in response to a second set of the at least one stimulus and a SCS treatment; and determine an efficacy of the SCS treatment by applying a classification algorithm on the first and second measurements of the at least two physiological parameters, obtained in response to the first and second set of at least one stimulus.

According to some embodiments, the system further comprises a stimulus evoking device configured to provide at least one stimulus to the subject.

According to some embodiments, the system further comprises a SCS device.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure. For the sake of clarity, some objects depicted in the figures are not to scale.

DETAILED DESCRIPTION

Figure 1A:
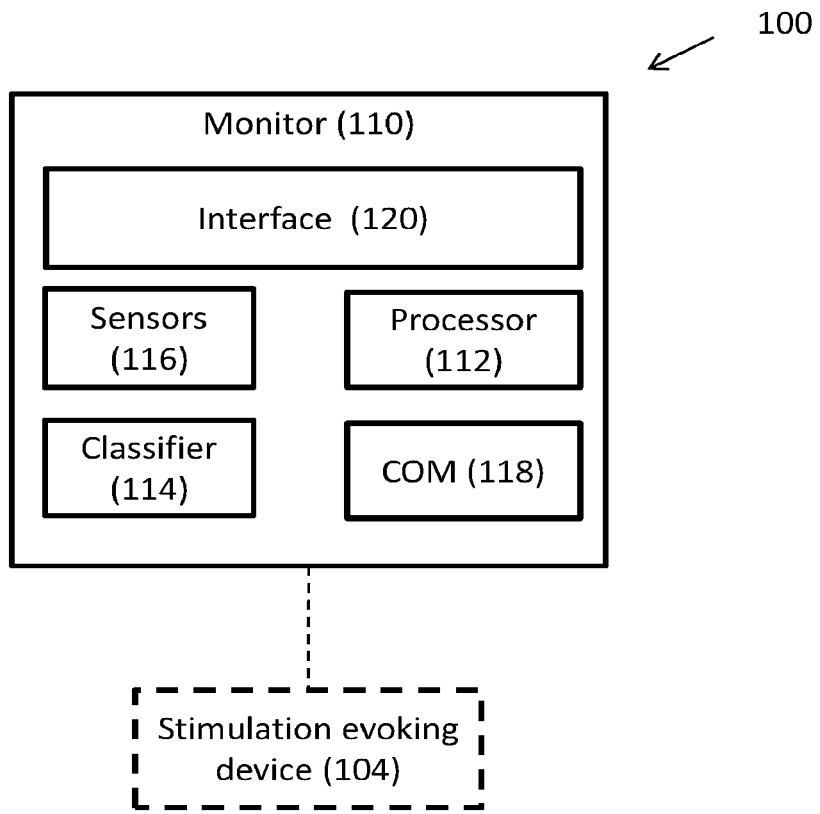
FIG. 1A schematically illustrates a system for determining chronic pain treatment efficacy, according to some embodiment.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

It is understood by one of ordinary skill of the art that the order of the methods as described should not be construed as sequential steps, and a different sequence of events may be envisaged.

According to some embodiments, there is provided a method for determining an efficacy of chronic pain treatment in a subject suffering from chronic pain. According to some embodiments, the method includes providing a first set of at least one stimulus to the subject; obtaining first measurements of at least two physiological parameters in response to the first set of at least one stimulus; providing a chronic pain treatment to the subject; providing a second set of at least one stimulus to the subject; obtaining second measurements of the at least two physiological parameters in response to the second set of at least one stimulus; and determining an efficacy of the chronic pain treatment by applying a classification algorithm on the first and second measurements of the at least two physiological parameters, obtained in response to the first and second set of at least one stimulus, respectively.

As used herein, the term "chronic pain" may refer to pain that persists for 6 months or longer and typically results from long-standing (chronic) medical conditions or actual or potential damage to the body. A number of symptoms can accompany chronic pain and can even arise as a direct result of the pain. These may include insomnia or poor quality sleep, irritability, depression and other mood changes, anxiety, fatigue, loss of interest in daily activities and may lead to disability. Chronic pain types can have somatic, visceral or neuropathic origin.

As referred to herein, the terms "patient" and "subject" may interchangeably be used and may relate to a subject suffering from chronic pain.

As used herein the term "efficacy" with regards to a chronic pain treatment may refer the degree of pain relief obtained due to the pain relief treatment. According to some embodiments, the efficacy may be presented as scores, index values, percentiles, probabilities or any other measure configured to intuitively presenting the efficacy of the treatment. Each possibility is a separate embodiment. According to some embodiment, the efficacy may be indicative of the likelihood of a subject benefitting from a particular chronic pain treatment.

According to some embodiments, the chronic pain treatment may include spinal cord stimulation (SCS). As used herein, the terms "spinal cord stimulation" and "SCS" may refer to neural stimulation by providing electrical pulses to the dorsal aspect of the spinal cord. According to some embodiments, the chronic pain treatment may include other types of neural stimulation for the treatment of chronic pain such as peripheral nerve stimulation, transcutaneous electrical nerve stimulation (TENS), sacral nerve stimulation or deep brain stimulation. Each possibility is a separate embodiment.

Additionally or alternatively, the chronic pain treatment may include analgesics medications, various injections such as nerve blocks, epidural injections or trigger point injections, physical treatments such as physiotherapy, acupuncture or more invasive therapies such as ablation, radio frequency treatments or spinal drug pumps implantation and the like. Each possibility is a separate embodiment.

As used herein, the terms "physiological parameter", "physiological features" and "extracted features" may be interchangeably used and may refer to at least one or more physiological feature that may be extracted and or derived from at least one physiological signal. The physiological parameter may be quantitative or qualitative. According to some embodiments, the physiological parameter may be derived from the physiological signal using feature extraction techniques and may include combining a plurality of extracted features and/or parameters, for example by non-linear regression techniques. Within the context of the present invention the terms "feature extraction", "feature processing" and "signal processing" may refer to the processes, manipulations and signal processing measures performed to analyze a physiological signal. Non-limiting examples of suitable physiological parameters are depicted in table 1, below.

TABLE 1 physiological parameters/features

| Number of features | Signal | Feature | Description |
|---|---|---|---|
| 15 | ECG | Q/R/S/T/P amplitude, average and variability | Amplitude, moving average amplitude and variability of amplitude of the Q/R/S/T/P pulse - an array that represent the location and the amplitude of the peak |
| 15 | ECG | RR/PQ/PR/QT/RS interval, average and variability | The interval, moving average of interval and variability of interval between each pulse or between internal pulse waves, an array that represent the location of the value computed, as the first peak location and its relevant interval |
| 1 | ECG | P wave width | Width of the P wave - an array that represent the location of the P peak and P wave relevant width |
| 1 | ECG | ST level | The point of inflection after S wave, which defines beginning of ST segment. An array that represent the location and point amplitude. |
| 5 | ECG | Q,R,S,T,P amplitude change | Derivative of the Amplitude |
| 5 | ECG | RR/PQ/PR/QT/RS interval change | Derivative of the pulses intervals |
| 1 | ECG | ST level change | Derivative of the ST level |
| 1 | ECG | QRS width change | Derivatives of width of the QRS complex |
| 1 | ECG | Energy of ECG residues | Computing the energy of the residues after applying the spectral cleaning and after applying auto regressive methods |
| 1 | ECG | Number of missing R peaks | Number of missing R-peaks for a certain time window |
| 4 | ECG Freq. | R-R Variability VLF,LF,MF and HF | Power (area) of the VLF, LF, MF and HF frequencies analysis of the interval variability between each pulse in a given resolution as was defined above in Heart Rate variability paragraph |
| 1 | ECG Freq. | R-R Variability LF/HH | Ratio between LF HRV power and HF HRV power |
| 1 | ECG Freq. | RRI Variability wavelet analysis | Wavelet analysis of the interval variability between each pulse in a given resolution. |
| 1 | ECG Freq. | alpha | Slope of HRV power spectrum |
| 1 | ECG Freq. | beta | Slope of the log of HRV PS |
| 3 | Respiratory | Upper peak values, average, variability | The peaks value, moving average of interval and variability of peaks amplitude. The peak represents the depth of respiration how deep we take a breath. |
| 3 | Respiratory | Lower Peak values, average, variability | The lower peaks value, moving average of interval and variability of peaks amplitude. The peaks represent the depth of breath release. |
| 3 | Respiratory | Respiratory rate, average and variability | The rate is 1/ Peak to peak distance. The interval rate, average rate and variability of the rate |
| 1 | Respiratory | Spectrum Analysis of the respiratory | Spectrum analysis of the respiratory signal |
| 1 | Respiratory | Power (area) | The area bellow the breath signal |

TABLE 1-continued physiological parameters/features

| Number of features | Signal | Feature | Description |
|---|---|---|---|
| 6 | PPG | PPG Peak and Trough Amplitude, average and variability | An array that represents location and amplitude of Peak and Trough. Peak denotes a point of maximum blood volume in a finger; Trough denotes a minimum basal blood volume. Both amplitude, moving average of the amplitude and variability are calculated |
| 1 | PPG | PPG maximum rate point | An array that represents location and amplitude of a point between onset injection and Peak where maximum rate of blood volume increase is observed |
| 1 | PPG | PPG dicrotic notch | An array that represents location and amplitude of PPG dicrotic notch. |
| 12 | PPG | PP/TT/NN/MM/ intervals, average and variability | Peak to peak, trough to trough, notch to notch, maximum rate to maximum rate, and other time intervals between points of interest in PPG beat. Both interval, moving average of the interval and variability are calculated - all representing the pulse rate |
| 12 | PPG | /PT/PN/NT/NM intervals, average and variability | peak to trough, peak to notch, notch to trough, notch to maximum rate, and other time intervals between points of interest in PPG beat. Both interval, moving average of the interval and variability are calculated |
| 5 | PPG | PP spectral analysis | Spectrum analysis of the Peak to Peak variability: HF, MF, LF and VLF bands power, LF/HF ration |
| 1 | PPG | Area Under Curve | An array that represents location and integral of single beat of PPG signal (AUC) |
| 1 | PPG | PPG envelope - time analysis | Time analysis of the envelope of PPG signal, (envelope - Peak-Trough of PPG signal) |
| 1 | PPG | PPG envelope - spectral | Spectral analysis of the envelope of PPG signal, (envelope - Peak- Trough of PPG signal) |
| 1 | PPG | PPG Variability wavelet analysis | Wavelet analysis of the interval variability between each pulse in a given resolution. |
| 1 | ECG-Resp | Respiratory sinus arrhythmia | Correlation between the Respiration and the decrease/increase in R-R interval |
| 1 | PPG-Resp | Respiratory sinus arrhythmia | Correlation between the Respiration and the decrease/increase in PPG intervals |
| 1 | ECG-BP | Pulse Transition time | An array that represent the location and the delay between R peak of ECG signal and Peak of Blood Pressure signal. (PTT or rPTT) (Weiss, et al. 1980) |
| 1 | ECG-PPG | Pulse Transition time | An array that represents the location and the delay between R peak of ECG signal and Peak of PPG signal (PTT or rPTT). |
| 1 | PPG-PPG | Pulse Transition time | An array that represents the location and the delay between two PPG signals located on the same arteriole in different (PTT or rPTT). |
| 1 | CNIBP | Average/variability mean aortic pressure (Pmean) | Average and variability (moving average and moving variability) |
| 6 | CNIBP | CBP Peak, and Trough amplitude, average and variability | An array that represents location and amplitude of Peak and Trough. Peak denotes the systolic BP; Trough denotes the diastolic. Amplitude, moving average amplitude and variability are calculated |
| 1 | CNIBP | Blood onset ejection point | An array that represents location and amplitude of a point after Trough where blood ejection is started (maximum second derivative) |
| 1 | CNIBP | CBP maximum rate point | An array that represents location and amplitude of a point between onset injection and Peak where maximum rate of blood volume increase is observed (middle of Anacrotic rise) |

TABLE 1-continued physiological parameters/features

| Number of features | Signal | Feature | Description |
|---|---|---|---|
| 1 | CNIBP | CBP dicrotic notch | An array that represents location and amplitude of CBP dicrotic notch. |
| 15 | CNIBP | PP/PT/PN/NT/NM intervals, average and variability | Peak to peak, peak to trough, peak to notch, notch to trough, notch to maximum rate, and other time intervals between points of interest in BP beat. |
| 1 | CNIBP | PP spectral analysis | Spectrum analysis of the Peak to Peak variability: HF, MF, LF and VLF bands power, LF/HF ration |
| 1 | CNIBP | Area Under Curve | An array that represents location and integral of single beat of PPG signal (AUC) |
| 1 | CNIBP | BP variability wavelet analysis | Wavelet analysis of the interval variability between each pulse in a given resolution. |
| 2 | GSR | Average/variability Perspiration | Average and variability of perspiration (moving average and moving variability) |
| 1 | GSR | Peak Interval, average and variability | The time interval between peaks, the moving average of the interval and the variability |
| 1 | GSR | Peak amplitude, average, variability | Amplitude, moving average amplitude and variability of amplitude of the GSR peaks comparing to the base band |
| 1 | GSR | General area | The area under each peak |
| 1 | GSR | Phasic EDA, amplitude average and variability | The first derivative of the GSR signal (EDA phasic), the moving average of the slopes (normal and absolute values) - mean phasic, and the variability of the slopes |
| 1 | GSR | spontaneous fluctuations Count | The average number of spontaneous fluctuations (SF) in an individual |
| 1 | GSR | Spectral Analysis: Peak Amplitude | The amplitude of the highest peak in the spectrum analysis |
| 1 | GSR | Spectral Analysis: Peak Frequency | The frequency of the highest peak in the spectrum analysis |
| 1 | GSR | Spectral Analysis: Power | The power (integration of signal) in the different frequency and specifically in 0.01-0.04Hz |
| 1 | GSR | difference between Peak Amplitude | The differences between the values of the highest peaks in the spectrum analysis of two different locations |
| 1 | GSR | GSR wavelet analysis | Wavelet analysis of the interval variability between each pulse in a given resolution. |
| 2 | Temperature | Average/variability Temperature | Average and variability of perspiration (moving average and moving variability) |
| 1 | Temperature | Peak Interval, average and variability | The time interval between peaks, the moving average of the interval and the variability |
| 1 | Temperature | Peak amplitude, average, variability | Amplitude, moving average amplitude and variability of amplitude of the temperature peaks comparing to the base band |
| 1 | Temperature | derivative amplitude average and variability | The first derivative of the temperature signal, the moving average of the slopes (normal and absolute values) and the variability of the slopes |

TABLE 1-continued physiological parameters/features

| Number of features | Signal | Feature | Description |
|---|---|---|---|
| 1 | Temperature | Spectral Analysis: Peak Amplitude | The value of the highest peak in the spectrum analysis |
| 1 | Temperature | Spectral Analysis: Peak Location | The frequency of the highest peak in the spectrum analysis |
| 1 | Temperature | Spectral Analysis Power | The power (integration of signal) in 0.01-0.04 Hz |
| 1 | Temperature | Temperature wavelet analysis | Wavelet analysis of the interval variability between each pulse in a given resolution. |
| 2 | EOG | Average/variability | |
| 4 | EEG/EMG | A, β, γ, δ, θ ratio between the powers | Classical EEG frequency band definitions. Frequency band Frequency range [Hz] delta, δ 0.5-4 - deep sleep (Sometimes is referred as 1-3.5) theta, θ 4-8 - drowsiness (Sometimes is referred as 3.5-8) alpha, α 8-14 - relaxed but alert (sometimes is referred as 8-13) beta, β 14-30 - highly alert and focused (sometimes is referred as 13-30) gamma γ, 30-70 - represent binding of different populations of neurons together into a network for the purpose of carrying out a certain cognitive or motor function (sometimes is referred as 36-100) |
| 1 | EEG/EMG | Average/variability | |
| 1 | EEG/EMG | median frequency | The frequency at which the median power is reached |
| 1 | EEG/EMG | mean frequency | The frequency at which the average power is reached |
| 1 | EEG/EMG | Mean power | The average power of the spectrum within epoch |
| 1 | EEG/EMG | Peak frequency | The frequency at which the power reaches its peak |
| 1 | EEG/EMG | Spectral Edge Frequency | The spontaneous EEG frequency below which x percent of the power are located. Typically x is in the range 75 to 95. SEF has variously been used to estimate the depth of anesthesia. For details see ( Bruhn, Ropcke and Hoeft 2000) |
| 1 | EEG/EMG | Approximate Entropy - | |
| 1 | EEG/EMG | BSR Burst Suppression ratio | The burst suppression ratio is the proportion of the suppression EEG in the analyzed epoch (usually one minute): $$BSR = \frac{\text{total time of suppression}}{\text{epoch length}} 100\%$$ |
| 1 | EEG/EMG | BcSEF | Burst compensated spectral edge frequency $$BcSEF = SEF\left(1 - \frac{BSR\%}{100\%}\right)$$ |
| 1 | EEG/EMG | WSMF | A generalized form of spectral edge frequency, referred to as weighted spectral median frequency (WSMF), edge frequency is calculated not necessarily from PSD but from amplitude spectrum, which is raised to the power p = [0.1 . . . 2.4]; second, the cutoff frequencies of the original spectrum are well-defined; and, third, factor r = [0:05 : : : 0:95] is used, the percentile of the spectrum (e.g., r = 0:5 for MF and r = 0:95 for SEF). |

TABLE 1-continued physiological parameters/features

| Number of features | Signal | Feature | Description |
|---|---|---|---|
| 1 | EEG/ EMG | CUP | Canonical univariate parameter: frequency bins with a width of 3 Hz or classical frequency bands are optimally weighted to obtain the best possible correlation with the drugs' effect-site concentration as obtained from pharmacokinetic-pharmacodynamic (PK-PD) modeling $$CUP = \sum_{k=1}^{10} 7k \log p_k$$ |
| 1 | EEG/ EMG | SpEn - | Spectral Entropy $$SpEn = -\sum_{k}^{N} p_k \log p_k.$$ |
| 1 | EEG/ EMG | BeSpEn - | Burst compensated Spectral Entropy $$BeSpEn = SpEn\left(1 - \frac{BSR(\%)}{100\%}\right).$$ |
| 1 | EEG/ EMG | Beta Ratio | $$BetaRatio = \log \frac{\hat{P}_{30-47\,Hz}}{\hat{P}_{11-20\,Hz}}.$$ |
| 4 | EEG/ EMG | Histogram parameters | Mean, Standard deviation, Kurtosis, Skewness of signal histogram |
| N | EEG/ EMG | AR parameters | Parameters of AR representation (Schlogl 2006) |
| 3 | EEG/ EMG | Normalized slope descriptors (Hjorth parameters) | NSD parameters can be defined by means of first and second derivatives. "Activity" is a measure of the mean power, "Mobility" is an estimate of the mean frequency and "Complexity" is an estimate of the bandwidth of the signal (frequency spread) (Hjorth 1973). |
| 3 | EEG/ EMG | Barlow parameters | Parameters based on Barlow EEG model which is an alternative time frequency decomposition. Parameters such as Running Mean Frequency and Spectral Purity Index (Goncharova and Barlow 1990) |
| 3 | EEG/ EMG | Wackermann parameters | Three multi-channel linear descriptors of EEG signal. spatial complexity ($\Omega$), field power ($\Sigma$) and frequency of field changes ($\Phi$) (Wackermann 1999) |
| 1 | EEG/ EMG | Brain rate | Weighted Mean Frequency (Pop-Jordanova and Pop-Jordanov 2005) |
| 1 | EEG/ EMG | SynchFastSlow | $$SynchFastSlow = \log \frac{\hat{B}_{40-47\,Hz}}{\hat{P}_{0.5-47\,Hz}}.$$ The spectrum and bispectrum, derived from two-second epochs, are smoothed using a running average against those calculated in the previous minute. 3 minutes window is required to obtain a consistent estimate of the bicoherence. |
| 1 | EEG/ EOG | 80 Hz frequency in EEG near the eyes | Ocular microtremor (OMT) is a constant, physiological, high frequency (peak 80 Hz), low amplitude (estimated circa 150-2500 nm) eye tremor. |
| 3 | EMG | Average/ variability/ and entropy | Average rectified value (mean of the absolute windowed signal) |
| 1 | EMG | Spectrum analysis - | Calculate the power of each frequency area - the location of the EMG should be defined |
| 1 | EMG | median frequency | The frequency at which the median power is reached |
| 1 | EMG | mean frequency | The frequency at which the average power is reached |
| 1 | EMG | Mean power | The average power of the spectrum within epoch |
| 1 | EMG | Peak frequency | The frequency at which the power reaches its peak |

TABLE 1-continued physiological parameters/features

| Number of features | Signal | Feature | Description |
|---|---|---|---|
| 1 | EMG | Mean power | The average power of the power spectrum within the epoch |
| 1 | EMG | Total power | The sum of the power spectrum within the epoch |
| 1 | EMG | spontaneous lower oesophageal contractions (SLOG) | Lower oesophageal contractility (LOC). The non-striated muscles in the lower half of oesophagus retain their potential activity even after full skeletal muscle paralysis by neuromuscular blocking agents. Spontaneous lower oesophageal contractions (SLOC) are non-propulsive spontaneous contractions mediated via vagal motor nuclei and reticular activating system in the brain stem. The frequency of these movements is increased as the dose of the anaesthetic is reduced. (Thomas and Evans 1989) |
| 1 | SVmR | Signal analysis | SVmR - skin vasomotor reflexes - using laser Doppler |
| 2 | Airway CO2 | Average/ Variability | End tidal Carbon Dioxid (anesthesia) |
| 1 | Airway Gases | Average | End tidal sevofluane (anesthesia) |
| 2 | Pneumoplethy smograph | Average/ Variability | PVR - Pulse Volume Recording - Average/Variability of signal's amplitude and signal analysis |
| N | All Signals | Change from the baseline of this patient | The baseline is computed during the fust minutes - when the patient is in a constant position reflecting the position of the treatment, with no pain stimuli. The differences (distance) of the parameters from this values are calculated (see 'Normalization per patient') |
| N | All Signals | Cross correlation/ Coherence/ canonical correlation | Cross correlation between all different signals canonical correlation |
| N | All Signals | Signature in time - functional features | Signature of a predefined period (for example 60 seconds of HR, EEG pattern, or other size of defined segment) |
| 12 | accelerometer X,Y,Z θ | Average value, Variability | accelerometer X,Y,Z theta, movement analysis |
| 1 | Environment Temperature | Value and moving average | |
| N | Environment parameters | | These features include all patient information that might affect the level of it stress response on the autonomous nervous system. It will mimic in a certain way the decision system that is activated, e.g., by the anesthesiologist when deciding when a patient under anesthesia might suffer from pain |
| 1 | Age | | |
| 1 | Gender | | |
| 1 | Weight | | |
| N | Disease | | Disease e.g. Sympathetic block |
| N | Disease Level | | For each of the above diseases define its level |
| N | Medication | | |
| N | Medicine Level | | For each of the above medication define its level (in mg per day/hour for example) |
| | Evoked pain | | Type of evoked pain: heat, cold, electric, tetanic, mechanic, pressure, touch, proprioception, chemical or the combination |

TABLE 1-continued physiological parameters/features

| Number of features | Signal | Feature | Description |
|---|---|---|---|
| | parameters | | Level of stimulus and duration<br>Mode of evoked pain: tonic, phasic,<br>Conditioned pain modulation (CPM), repeat, combined<br>Location: painful area, non-painful area, combination |
| | SCS parameters | | On/off, stimulation frequency, duration, pulse width, intensity, waveform, wave pattern, signal, amplitude, onset timing, delay, treatment length, treatment period, onset delay |

As used herein, the term "at least two" with referral to physiological parameters may include 2, 3, 4, 5, 6, 7, 8, 9, 10 or more physiological parameters. Each possibility is a separate embodiment. According to some embodiments, the at least two parameters may refer to a plurality of parameters. As used herein, the term "plurality" may refer to 4 or more, 5 or more, or 10 or more parameters. Each possibility is a separate embodiment.

As used herein, the term "physiological signal" may refer to any measurable signal or event that is measured directly or indirectly from a subject through sensors, transducers or the like. According to some embodiments, the physiological signals may be further analyzed, processed, or otherwise manipulated to provide further details regarding the state of a patient. According to some embodiment, the physiological signal may be processed to derive physiological parameters.

Non-limiting examples of physiological signals include blood pressure (BP), respiration, internal and/or surface temperature, pupil diameter, galvanic skin response (GSR), and signals received and/or derived from electrocardiography (ECG), photoplethysmography (PPG), electrooculography (EOG), electroencephalography (EEG), electromyography (EMG), frontalis electromyogram (FEMG), laser Doppler velocimetry (LDV), dynamic light scattering (DLS), near-infrared spectroscopy (NIRS), partial pressure of carbon dioxide, and accelerometers or any portion or combination thereof. Preferably a physiological signal may further comprise any signal that is measureable and/or detectible from a subject.

According to some embodiments, the identification may be based on parameters extracted from at least PPG and GSR signals and may for example include PPG amplitude, PPG amplitude variation, pulse rate (PR) interval, PR variability and GSR fluctuations. According to some embodiments, the parameters may be combined using non-linear regression. According to some embodiments, the identification may further be based on parameters extracted from accelerometer readings.

As used herein, the term "at least one" with referral to physiological signals may include 1, 2, 3, 4, 5 or more physiological signals. Each possibility is a separate embodiment.

As used herein, the terms "physiological response" and "physiological status" may refer to a pattern and/or value obtained for the at least one physiological signal and/or the at least two physiological parameters derived therefrom, for example in response to a stimulus and/or in response to a SCS treatment.

As used herein, the term "Pupil Diameter Measurement (PD)" may refer to measurements of pupil size and movement. PD may be measured by infrared videography or computerized pupillometry.

As used herein, the term "Electromyography (EMG)", refers to a technique for recording and evaluating physiologic properties of muscle activity either at rest or while contracting. EMG signals may be recorded through surface electrodes. A plurality of location specific EMG signals may be recorded from various locations on a subject and/or muscle groups. For example Frontalis (scalp) Electromyogram (FEMG) measures the frontalis muscle underlying the forehead.

As used herein, the term "Photo PlethysmoGraph (PPG)" may refer to a non-invasive transducer configured to measure relative changes of blood volume from a finger or from other different body locations (finger, hand, earlobe, forehead. forearm, etc.)

As used herein, the term "Electro-Cardio-Gram (ECG)" may refer to non-invasive recordings of the electrical activity of the heart.

As used herein, the term "ElectroEncephaloGram (EEG)" may refer to non-invasive readings of the electrical activity of the brain, as recorded from electrodes placed on the scalp.

As used herein, the term "ElectrogastroenteroGram (EGG)" may refer to non-invasive readings of the electrical activity of the stomach, and the intestines.

As used herein, the term "Galvanic Skin Response (GSR)" may refer to non-invasive readings of the electrical conductance or resistance of the skin, which varies depending on the amount of sweat-induced moisture on the skin. Also known as Skin conductance, electro-dermal response (EDR), skin conductance response (SCR) and Galvanic skin resistance.

As used herein, the term "ElectroOculaGraph (EOG)" may refer to non-invasive recordings of electrical activity produced by eye movement and retina, as recorded from electrodes placed on the face and frontal lobe.

As used herein, the term "Blood pressure (BP)", may refer to arterial blood pressure, i.e., to the force exerted by circulating blood on the walls of the larger arteries. BP may be measured by invasive or non-invasive methods and can be read continuously (Continuous Non Invasive Blood Pressure—CNIBP) or discretely (NIBP).

As used herein, the term "Laser Doppler Velocimetry (LDV)" may refer to quantification of blood flow in tissues such as the skin. LVD may enable calculation of parameters such as vasomotor reflex (SVMR).

As used herein, the term "Capnography" may refer to measurements of concentration or partial pressure of carbon dioxide ($CO_2$). Other measurements on expiratory gases may also be determined for example concentration end-tidal nitrous oxide ($N_2O$), oxygen ($O_2$), or anesthetic agents.

As used herein, the term "Accelerometer" may refer to a device for measuring movement, acceleration and gravity induced reaction forces.

According to some embodiments, the at least one stimulus may include: a painful stimulus on non-painful area, painful stimulus on painful area, non-painful stimulus on non-painful area, non-painful stimulus on painful area. Each possibility is a separate embodiment. According to some embodiments, the at least one stimulus may include lack of stimulus.

As used herein, the term "at least one" with referral to stimulus may include 1, 2, 3, 4 or more stimuli. Each possibility is a separate embodiment.

According to some embodiments, the source of the at least one stimulus is selected from tetanic stimulus, thermal (heat or cold) stimulus, pressure stimulus, touch (tickle, itch, crude, flutter, pressure) stimulus, electric stimulus, mechanical stimulus, proprioception stimulus, chemical stimulus or combinations thereof. Each possibility is a separate embodiment. According to some embodiments, if more than one stimulus is applied, the stimuli may be of same or different source.

According to some embodiments, the at least one stimulus may be varied. Suitable variations of the at least one stimulus include but are not limited to: type of stimulation, location of stimulation, duration, intensity, or combinations thereof. Each possibility is a separate embodiment. According to some embodiments, the stimulation may be controllable and repeatable. According to some embodiments, the stimulation may facilitate classification and evaluation of the efficacy of SCS treatment protocol. According to some embodiments, the stimulation may facilitate classification and evaluation of the efficacy of a nerve stimulation protocol.

According to some embodiments, the painful stimulus and the non-painful stimulus may be a same source of stimulus applied at a different intensity. According to some embodiments, the painful stimulus and the non-painful stimulus may be of a different source.

According to some embodiments, determining the efficacy of the chronic pain treatment, such as SCS treatment, includes determining a level of pain, before and after the treatment, based on a mathematical integration of the at least two physiological parameters obtained in response to each of the first and second sets of at least one stimulus. According to some embodiments, the mathematical integration includes applying linear regression. According to some embodiments, the mathematical integration includes applying classification algorithms.

According to some embodiments, applying the classification algorithm may include directly or indirectly comparing the first and second measurements to pre-stored data sets of measurements obtained from subjects with known chronic pain treatment efficacies. According to some embodiments, the pre-stored data set includes measurements of the at least two parameters and/or at least one physiological signal from which the at least two parameters can be derived. According to some embodiments, the pre-stored data set includes measurements of the at least two parameters and/or at least one physiological signal, obtained prior to and/or after a chronic pain treatment (such as SCS treatment). According to some embodiments, the pre-stored data set includes measurements of the at least two parameters and/or the at least one physiological signal, obtained prior to and/or after introduction of a stimulus, as essentially described herein.

According to some embodiment, applying the classification algorithm may include utilizing a classification technique. Non-limiting examples of classification techniques include: Nearest Shrunken Centroids (NSC), Classification and Regression Trees (CART), ID3, C4.5, Multivariate Additive regression splines (MARS), Multiple additive regression trees (MART), Nearest Centroid (NC) classifier, Shrunken Centroid Regularized Linear Discriminate and Analysis (SCRLDA), Random Forest, ensemble decision trees, ensemble regression trees, bucket of models, Boosting, Bagging Classifier, AdaBoost, RealAdaBoost, LPBoost, TotalBoost, BrownBoost, MadaBoost, LogitBoost, GentleBoost, RobustBoost, Support Vector Machine (SVM), kernelized SVM, Linear classifier, Quadratic Discriminant Analysis (QDA) classifier, Naive Bayes Classifier, Generalized Likelihood Ratio Test (GLRT) classifier with plug-in parametric or non-parametric class conditional density estimation, k-nearest neighbor, Radial Base Function (RBF) classifier, Multilayer Perceptron classifier, Bayesian Network (BN) classifier, combinations, ensembles and stacking thereof or any other suitable classification techniques known in the art. Each possibility is a separate embodiment.

According to some embodiment, applying the classification algorithm may include using a classifier adept at multiclass classification. According to some embodiment, multi-class classification may be adapted from binary classifiers as is known and accepted in the art. According to some embodiment, the binary classifiers may be adapted to perform a multi-class classification by reducing the multi-class problem to a plurality of multiple binary problems using methods as is known and accepted in the art, for example but not limited to, one-vs-one with voting schemes by majority vote or pairwise coupling, one-vs-rest, Error Correcting Output Codes, or any combination thereof. Each possibility is a separate embodiment.

According to some embodiments, applying the classification algorithm may include applying a hierarchical multi-class classification. According to some embodiments, the hierarchical multi-class classification may be performed as a tree structure having a single parent class. According to some embodiments, the hierarchical multi-class classification may be performed as a tree structure having acyclic graph structure with at least one parental class.

According to some embodiments, applying the classification algorithm may include applying a trained classifier. According to some embodiments, the classifier may be trained on a "training set" such as pre-stored data sets obtained from subjects with known chronic pain treatment efficacies, as essentially descried herein. According to some embodiments, the training set may include data for classification that is made available from publicly available databases, proprietary clinical trials data, on site recorded data from at least one or more subject or combinations thereof. Each possibility is a separate embodiment. According to some embodiments, the training set includes input and output signals that mimic the input and output signals of the classifier described herein. According to some embodiments, the training set includes input signals similar in nature to the expected input, of a classifier according to the present invention. According to some embodiments, the training set input signals comprise data similar to the physiological parameters disclosed herein. According to some embodiments, the output signals comprising the training set are similar in nature to the expected output from a classifier, according to the present invention. According to some embodiments, the training set is compiled by a pain expert for example a physician or other skilled person in the art of pain detection. According to some embodiments, the training set is compiled during a clinical trial comprising controlled pain stimuli.

As used herein, the term "learning" and "training" may refer to training a classifier and/or classifying algorithm on a data set having known input (for example physiological parameters and/or combinations of physiological parameters) and output values (treatment efficacy), in order to extrapolate from previously unseen input data an expected output value.

According to some embodiments, applying the classification algorithm may further include taking into consideration demographic data. Non-limiting examples of demographic data include age, gender, ethnicity, marital status, weight, BMI, height or any other suitable demographic data. Each possibility is a separate embodiment.

According to some embodiments, applying the classification algorithm may further include taking into consideration a priori clinical. Non-limiting examples of a priori clinical data include nociception response to painful stimuli and/or to background chronic pain, conceptual response, context relevance response, behavioral response, subject history, type of prescribed medicine, diagnostics, patient condition, patient definition of pain level, location of SCS device, drug history, drug interaction or any other clinically relevant data. Each possibility is a separate embodiment. According to some embodiments, including demographic and/or a priori data may increase the classification efficiency.

According to some embodiments, providing a chronic pain treatment may include providing a trial treatment. As used herein, the term trial treatment may refer to a short term and/or temporary treatment configured for evaluation of a permanent and/or long term treatment. As used herein the terms "short term treatment" and "temporary treatment" may include a treatment provided for 6 months or less, 2 months or less, 1 month or less, 2 weeks or less, 1 week or less, 3 days or less, 2 days or less, 1 day or less, or less than one day. Each possibility is a separate embodiment. As used herein the term "long term treatment" may include a treatment provided for more than 1 month, more than 2 month, or more than 6 months. Each possibility is a separate embodiment. According to some embodiments, the long term treatment may be a permanent treatment.

According to some embodiments, the trial treatment may include proving a short term treatment with a medicament, such as but not limited to an analgesic. According to some embodiments, the trial treatment may be a temporary SCS (trial SCS). According to some embodiments, providing a temporary SCS may include implanting into the subject a spinal cord stimulator comprising stimulating electrodes only. According to some embodiments, providing a temporary SCS may include a spinal cord stimulator without implanting an electrical pulse generator.

According to some embodiments, the method may further include predicting a treatment efficacy of a permanent chronic pain treatment, based on the determined efficacy of a trial treatment. According to some embodiments, the method may further include providing a treatment recommendation based on the predicted treatment efficacy. According to some embodiments the treatment recommendation may be a recommendation to continue or discontinue the chronic pain treatment. For example, the treatment recommendation may be to implant a permanent SCS device. For example, the treatment recommendation may be a recommendation not to implant a permanent SCS device. According to some embodiments the treatment recommendation may be providing a chronic pain treatment protocol, such as but not limited to a SCS treatment protocol According to some embodiments, the treatment protocol may include recommended treatment settings, such as but not limited to recommended settings of SCS parameters.

According to some embodiments, the method may include predicting efficacy of permanent SCS implantation based on the determined efficacy of a trial SCS. As used herein, the term "permanent SCS" may refer to implantation of stimulating electrodes together with an electrical pulse generator.

According to some embodiments, the chronic pain may include Failed Back Surgery Syndrome (FBSS), complex regional pain syndrome (CRPS), Radiculopathy, Peripheral Vascular Disease (PVD), neuralgia, neuropathic pain, refractory angina pectoris (RAP), Ischemic pain or combinations thereof. Each possibility is a separate embodiment.

According to some embodiments, there is provided a system for determining efficacy of a chronic pain treatment. According to some embodiments, the system includes a processor configured to obtain a first measurement of at least two physiological parameters in response to a first set of at least one stimulus; obtain a second measurements of the at least two physiological parameters in response to a second set of the at least one stimulus and a chronic pain treatment; and determine an efficacy of the chronic pain treatment by applying a classification algorithm on the first and second measurements of the at least two physiological parameters, obtained in response to the first and second set of at least one stimulus.

According to some embodiments, the chronic pain treatment may be SCS treatment. According to some embodiments, the chronic pain treatment may be nerve stimulation, such as but not limited to transcutaneous electrical nerve stimulation (TENS), sacral nerve stimulation or tibial nerve stimulation. Each possibility is a separate embodiment.

According to some embodiments, the system further includes at least one sensor configured to sense (directly or indirectly), at least one physiological signal. According to some embodiments, the at least two physiological parameters may be derived from the at least one physiological signal sensed by the at least one sensor.

As used herein, the term at least one, with referral to sensors may include 1, 2, 3, 4 or more sensors. Each possibility is a separate embodiment. It is thus understood, that the at least two physiological parameters may be derived from a same sensor and/or from different sensors. As a non-limiting example, the at least two physiological parameters may include 3 physiological parameters, one parameter derived from an accelerometer and two physiological parameters derived from a PPG sensor.

According to some embodiments, the system may further include a stimulus evoking device configured to provide at least one stimulus to the subject. Non-limiting examples of suitable stimulus evoking devices include Von Frey Filaments, and Peltier surface stimulator. Each possibility is a separate embodiment.

According to some embodiments, the system may further include a communication module. According to some embodiments, the communication module may be configured to optionally wirelessly communicate the determined efficacies of the chronic pain treatment to the subject, a caregiver, and/or to a communication device such as but not limited to a mobile telephone, a smartphone, a medical device, a server, a health care provider database, a database, a health care provider server, a SCS stimulation device, a nerve stimulation device, or any combination thereof. Each possibility is a separate embodiment.

According to some embodiments, the system may further include a patient interface such as but not limited to a keyboard and/or a visual display, or the like.

According to some embodiments, the system may further include a spinal cord stimulator. According to some embodiments, the system may further include a nerve stimulator.

According to some embodiments, there is provided a method for calibrating and/or adjusting spinal cord stimulation (SCS) treatment in a subject, the method comprising: providing a SCS being characterized by at least one SCS parameters; varying a value of one of the at least one SCS parameters along a dynamic range thereof; obtaining measurements of at least two physiological parameters in response to varying the value of the one SCS parameter along the dynamic range thereof; determining an efficacy of the SCS along the dynamic range of the varied SCS parameter by applying a classification algorithm to the at least two physiological parameters obtained in response to varying the one SCS parameter along the dynamic range thereof; and selecting the value of the one SCS parameter yielding the highest efficacy.

According to some embodiments, the method further comprises providing at least one stimulus to the subject. According to some embodiments, the at least one stimulus may be provided prior to while and/or after varying the SCS parameter along its dynamic range. Each possibility is a separate embodiment.

According to some embodiments, obtaining measurements of at least two physiological parameters in response to the SCS, having a SCS parameter varied along its dynamic range, may include obtaining a plurality of measurements each obtained for a different value the varied SCS parameter. As used herein, the term "plurality" may refer to more than 2 measurements, such as 3, 4, 5, 10, 100 or more measurements. Each possibility is a separate embodiment.

According to some embodiments, obtaining measurements of the at least two physiological parameters while changing the SCS parameter along its dynamic range may include continuously obtaining measurements of the at least two physiological parameters, while changing the value of the SCS parameter along its dynamic range. According to some embodiments, the remaining parameters of the at least one SCS parameter may be fixed while the one parameter is varied along its dynamic range.

According to some embodiments, the at least one SCS parameter may include type of stimulation, stimulation frequency, duration, pulse width, intensity, waveform, wave pattern, signal, amplitude, onset timing, delay, treatment length, treatment period, onset delay or any combination thereof. Each possibility is a separate embodiment.

As used herein, the term "dynamic range" with regards to a SCS parameter may refer to any range of values ranging from minimum to maximum of a given parameter.

According to some embodiments, varying the SCS parameter along its dynamic range may include making continuous, incremental and/or step wise changes in the value of the SCS parameter. Each possibility is a separate embodiment.

As used herein, the term "at least one" with referral to SCS parameters may include 1, 2, 3, 4 or more SCS parameters. Each possibility is a separate embodiment.

According to some embodiments, the method may further include determining an optimal treatment protocol. According to some embodiments, the optimal treatment protocol may include a treatment protocol in which all of the at least one SCS parameter have been adjusted and/or calibrated to provide a highest efficacy.

According to some embodiments, the method further includes communicating the optimal treatment protocol to the subject and/or to a caregiver thereof. According to some embodiments, communicating the optimal treatment protocol may include wireless communication of the treatment protocol. According to some embodiments, the communicating may refer to using cellular, internet, bluetooth, optical, IR, RF, ultrasound, Near-field communication, or any other suitable communication means. Each possibility is a separate embodiment.

According to some embodiments, there is provided a method for calibrating and/or adjusting nerve stimulation in a subject, the method comprising: providing a nerve stimulation being characterized by at least one nerve stimulation parameter; varying a value of one nerve stimulation parameter along a dynamic range thereof; obtaining measurements of at least two physiological parameters in response to varying the value of the one nerve stimulation parameter along the dynamic range thereof; determining an efficacy of the nerve stimulation along the dynamic range of the varied nerve stimulation parameter by applying a classification algorithm to the at least two physiological parameters obtained in response to varying the one nerve stimulation parameter along the dynamic range thereof; and selecting the value of the one nerve stimulation parameter yielding the highest efficacy.

According to some embodiments, the nerve stimulation may be selected from spinal cord stimulation, transcutaneous electrical nerve stimulation (TENS), sacral nerve stimulation or tibial nerve stimulation or combinations thereof. Each possibility is a separate embodiment.

According to some embodiments, the method further comprises providing at least one stimulus to the subject. According to some embodiments, the at least one stimulus may be provided prior to while and/or after varying the nerve stimulation parameter along its dynamic range. Each possibility is a separate embodiment.

According to some embodiments, obtaining measurements of at least two physiological parameters in response to the nerve stimulation, having a nerve stimulation parameter varied along its dynamic range, may include obtaining a plurality of measurements each obtained for a different value of the varied nerve stimulation parameter. As used herein, the term "plurality" may refer to more than 2 measurements, such as 3, 4, 5, 10, 100 or more measurements. Each possibility is a separate embodiment.

According to some embodiments, obtaining measurements of the at least two physiological parameters while changing the nerve stimulation parameter along its dynamic range may include continuously obtaining measurements of the at least two physiological parameters, while changing the value of the nerve stimulation parameter along its dynamic range. According to some embodiments, the remaining parameters of the at least one nerve stimulation parameters may be fixed while the one nerve stimulation parameter is varied along its dynamic range.

According to some embodiments, the at least one nerve stimulation parameter may include type of stimulation, stimulation frequency, duration, pulse width, intensity, waveform, wave pattern, signal, amplitude, onset timing, delay, treatment length, treatment period, onset delay or any combination thereof. Each possibility is a separate embodiment.

As used herein, the term "dynamic range" with regards to a nerve stimulation parameter may refer to a range of values ranging from minimum to maximum of a given parameter.

According to some embodiments, varying the nerve stimulation parameter along its dynamic range may include making continuous, incremental and/or step wise changes in the value of the nerve stimulation parameter. Each possibility is a separate embodiment.

As used herein, the term "at least one" with referral to nerve stimulation parameters may include 1, 2, 3, 4 or more nerve stimulation parameters. Each possibility is a separate embodiment.

According to some embodiments, the method may further include determining an optimal treatment protocol. According to some embodiments, the optimal treatment protocol may include a treatment protocol in which all of the at least one nerve stimulation parameters have been adjusted and/or calibrated to provide a highest efficacy.

According to some embodiments, the method further includes communicating the optimal treatment protocol to the subject and/or to a caregiver thereof. According to some embodiments, communicating the optimal treatment protocol may include wireless communication of the treatment protocol. According to some embodiments, the communicating may refer to using cellular, Internet, bluetooth, optical, IR, RF, ultrasound, near-field communication, or any other suitable communication means. Each possibility is a separate embodiment.

According to some embodiments, there is provided a system for adjusting and/or calibrating spinal cord stimulation (SCS) in a subject, the system comprising a processor configured to receive measurements of at least two physiological parameters obtained in response to varying a SCS parameter along a dynamic range thereof; determine an efficacy of the SCS along the dynamic range of the varied SCS parameter by applying a classification algorithm to the at least two physiological parameters obtained in response to varying the one SCS parameter along the dynamic range thereof; and selecting the value of the one SCS parameter yielding the highest efficacy.

According to some embodiments, the processor may further be configured to control the at least one SCS parameter. According to some embodiments, controlling the at least one SCS parameter may include varying the parameter along the dynamic range thereof. According to some embodiments, each parameter is varied separately. According to some embodiments, the processor may be configured to automatically vary each of the at least one SCS parameter along its dynamic range until each of the at least one SCS parameters, alone and/or in combination yield a highest efficacy. According to some embodiments, the processor may be configured to automatically vary each of the at least one SCS parameter when SCS efficacy reaches a predetermined threshold value.

According to some embodiments, the system may further include a communication module. According to some embodiments, the communication module may be configured to optionally wirelessly communicate the determined efficacies of the chronic pain treatment to the subject, a caregiver, and/or to a communication device, such as but not limited to, a mobile telephone, a smartphone, a medical device, a server, a health care provider database, a database, a health care provider server, a SCS stimulation device, or any combination thereof. Each possibility is a separate embodiment.

According to some embodiments, the system may further include a patient interface, such as but not limited to, a keyboard and/or a visual display, or the like.

According to some embodiments, the system may further include a SCS device.

Reference is now made to FIG. 1A which is a schematic block diagram of an optional monitoring system 100 for determining an efficacy of spinal cord stimulation (SCS) for a subject with chronic pain.

System 100 includes monitor 110 configured to obtain and analyze measurements of at least one physiological signal and to determine efficacy of spinal cord stimulation (SCS) for a subject based on the analyzed signals. Monitor 110 includes a processing module 112, a classifier module 114, a sensor module 116, and a communication module 118. Monitor 110 may optionally further include an interface module 120.

Processing module 112 preferably comprises a processor and necessary memory and power supply capabilities for controlling and rendering monitor 110 functional. Optionally processing module 112 may render monitor 110 functional within a cloud computing environment.

Classifier module 114 is configured to provide classification of at least two physiological parameters derived from the at least one physiological signal. Preferably classification module 114 facilitates computation and processing associated with the classification of pain. Classification module 114 may for example provide for signal processing, normalization, feature extraction and classification. According to some embodiments, classifier module 114 is adept at classifying and identifying chronic pain that is conducive for spinal cord stimulation treatment with a spinal cord stimulation device 102, (shown in FIG. 1B). Optionally and preferably module 114 further provides for determining the efficacy of SCS treatment in a particular subject. The objective evaluation of SCS efficacy and/or the physiological status of the subject is facilitated and/or based on processing of the at least one physiological signal with classification module 114. According to some embodiments, classification module 114 enables identifying and classifying the at least one physiological signal monitored with device 110 by utilizing a plurality of processing techniques and classifiers. Optionally the at least one physiological signal is processed and utilized to identify and classify at least two physiological parameters into classes that identify individuals that may have positive results in pain management with a SCS device 102. Optionally such classification may be further processed to provide an evaluation of the efficacy of treating chronic pain with a SCS device for a particular individual. According to some embodiments, classifier 114 may be an integral part of processor 112.

Sensor module 116 includes at least one sensor configured to non-invasively sense and record at least one physiological signal from a patient. Suitable sensors and physiological signals have been described herein. Optionally, the at least one physiological signal may be pre-processed and processed, with classification module 114, facilitating the detection and classification of at least two physiological parameters and/or a SCS status for example with combined working of processing module 112 and classification module 114. Classification related to SCS treatment may be based on a plurality of features and/or parameters extracted from at least one physiological signal, for example parameters extracted from PPG and GSR signals and may include but are not limited to PPG amplitude, PPG amplitude variation, pulse rate, PR variability and GSR fluctuations. Optionally, the physiological parameters may be combined using non-linear regression to provide for identifying individuals that may benefit from SCS treatment.

Optionally monitor 110 may further be configured to provide an optimal spinal cord stimulation treatment protocol based on the detection, processing and classification, of the at least one physiological signal. According to some embodiments, the optimal SCS treatment protocol may include optimal settings for at least one SCS parameter, such as but not limited to, the type of stimulation, stimulation frequency, duration, pulse width, intensity, waveform, wave pattern, signal, amplitude, onset timing, delay, treatment length, treatment period, onset delay, the like or any combination thereof.

Communication module 118 is configured to communicate and exchange data with optional external devices and/or processing units, such as but not limited to, a display, a computer, a mobile a communication device, a mobile telephone, a smartphone, a medical device, a server, a health care provider database, a database, a health care provider server, a SCS stimulation device, or any combination thereof. Communication module 118 may communicate by any means known in the art, such as but not limited to, wireless, wired, cellular, internet, Bluetooth, optical, IR, RF, ultrasound, near field communication, the like or any combination thereof.

Interface module 120 is configured to interfacing with monitor 110. Optimally interface module 120 may be provided in the form of a human interface and/or display, such as a keyboard and/or a visual display, or the like. Optionally interface module 120 may be provided in the form of a machine to machine interface for example provided in the form of a USB drive hub, a magnetic scanner, a magnetic card scanner, a memory drives, flash memory drive, volatile memory, non-volatile memory, memory port, mobile memory port and/or drive, or the like. Each possibility is a separate embodiment.

Monitor 110 may be non-invasively associated with an individual experiencing chronic pain, where monitoring may be provided by sensor module 116 and classifier module 114 to identify if the individual may benefit from SCS treatment. Optionally monitor 110 may be configured to identify individuals that may benefit from SCS treatment by identifying a particular set of features extracted from the sensed physiological signals.

Optionally, identifying individuals that may benefit from SCS treatment using monitor 110 may further include incorporating offline data for example a priori data, as essentially described herein. Optionally such offline and/or a-priori data may be utilized to facilitate classification with classifier module 114. Optionally a priori data may be communicated to monitor 110 via communication module 118 and/or via interface module 120.

Optionally system 100 may further include or be associated with a stimulation evoking device 104 provided for externally stimulating an individual for example by evoking a physiological response that may then be monitored and measured with monitor 110. Stimulation evoking device 104 may be configured to evoke a stimulation, such as but not limited to: a pain evoking stimulation, inert stimulation, a non-pain evoking stimulation, painful stimulation, non-painful stimulation, background pain, tonic stimulation, phasic stimulation, conditioning pain modulation, mechanical induced pain, electric induced pain, tetanic induced pain, thermal induced pain, proprioception induced pain, chemical induced pain, pressure induced pain, the like or any combination thereof. Each possibility is a separate embodiment. Optionally, stimulation evoking device 104 may be utilized to provide controllable and repeatable stimulation that may be varied according to at least one or more parameters for example including, but not limited to the type of stimulation, location of stimulation, duration, intensity, or the like parameters. Each possibility is a separate embodiment. Optionally stimulation evoking device 104 may be Von Frey Filaments, Peltier surface stimulator, heat or cold thermode, algometer, tetanic stimulator or any other suitable stimulation evoking device. Optionally, stimulation evoking device 104 is configured to provide controllable and repeatable stimulation which facilitates classification and evaluation of the efficacy of a SCS treatment protocol using monitor 110.

Figure 1B:
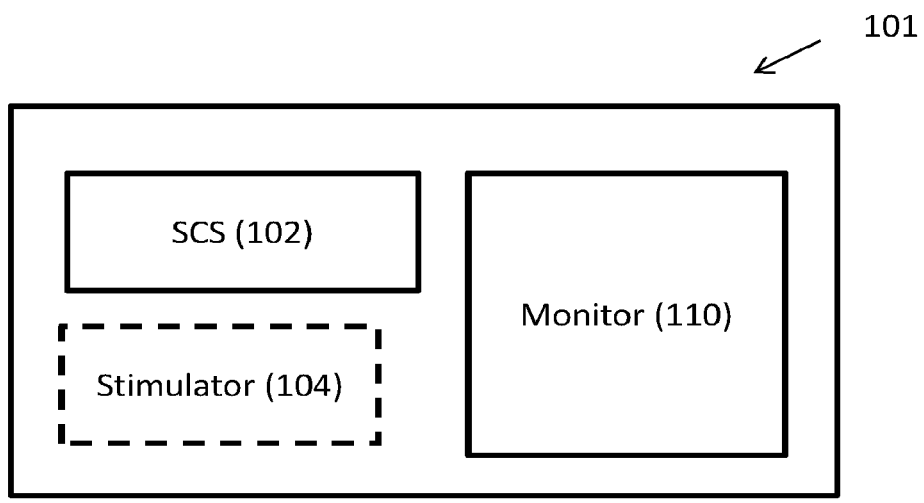
FIG. 1B schematically illustrates a system for determining chronic pain treatment efficacy, according to some embodiment.

Reference is now made to FIG. 1B showing system 101 comprising monitor 110 as previously described with respect to FIG. 1A, and a SCS device 102 adapted to provide SCS treatment. Optionally system 100 may further include stimulation evoking device 104, as described above. SCS device 102 may be a standard device that may be provided in the form of a temporary SCS device or an implantable permanent SCS device. Optionally SCS device 102 may be in wired and/or wireless communication with monitor 110, for example via communication module 118, as described in FIG. 1A above. Optionally, a temporary SCS device may be tested with monitor 110 to evaluate the efficacy of SCS treatment for an individual, for example as described in further detail in FIG. 2B prior to implanting a permanent SCS device.

Monitor 110 is configured to detect and/or evaluate the efficacy of a SCS treatment provided by SCS device 102. According to some embodiments, monitor 110 acquires at least one physiological signal from which at least two physiological parameters are derived, while controlling the stimulation provided with the SCS device 102. Stimulation provided by SCS device 102 may be controlled at various levels, for example ON/OFF states, as well as settings of stimulation parameters, as essentially described herein. As a non-limiting example, a subject suffering from chronic pain may be assessed for his/hers likelihood of benefitting from SCS. The subject is associated with SCS device 102 and monitor 110, where monitor 110 objectively measures the SCS efficacy and/or enables analysis of the level of at least two physiological parameters extracted from at least one physiological signal acquired by monitor 110, while SCS device 102 provides SCS stimulation. Monitor 110 may identify and/or classify the efficacy of SCS treatment by acquiring and processing at least one physiological signal obtained from the individual while the SCS device 102 is controllably placed in an ON or OFF state. For example, while device SCS 102 is in the ON state, monitor 110 will objectively measure and/or identify and classify the level of at least two physiological parameters correlated with the ON state. Similarly, while SCS device 102 is in the OFF state, monitor 110 will objectively measure and/or identify and classify the level of at least two physiological parameters correlated with the OFF state. Monitor 110 may then enable evaluation the efficacy of SCS treatment based on a comparison of the level of at least two physiological parameters determined for the ON and OFF states, respectively.

According to some embodiments, in addition to and/or instead of the ON/OFF state evaluation, the level of at least two physiological parameters may be determined while controllably alternating stimulation parameters to determine the optimal stimulation required for alleviating the pain.

According to some embodiments, monitor 110 provides an efficacy evaluation of SCS following implantation of a temporary SCS device to identify if an individual is suitable for permanent implantation, as essentially described herein.

According to some embodiments, stimulation evoking device 104 may be utilized to provide controlled and repeatable stimulation, as previously described. For example, a physiological response pattern of a subject may be evaluated by providing stimulation to the subject using pain evoking device 104 while SCS device 102 is either in its ON or OFF state.

Figure 2A:
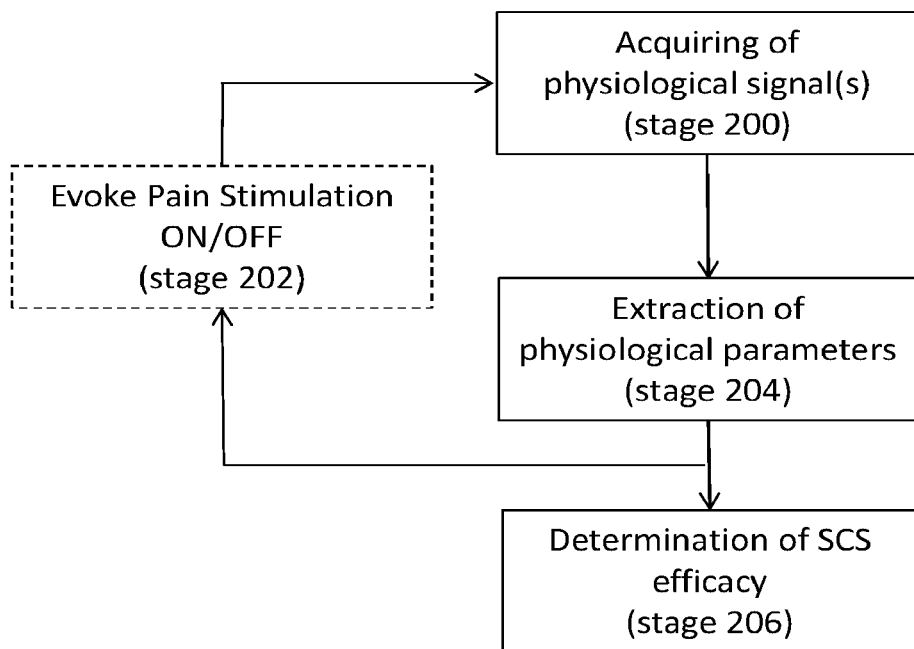
FIG. 2A is a flowchart of an exemplary method, according to some embodiment.

Reference is now made to FIG. 2A which is an illustrative flowchart of a method for determining an efficacy of spinal cord stimulation (SCS) for a subject with chronic pain. The efficacy of SCS may be determined without employing a SCS device, but rather based on acquiring at least one physiological signal using a monitor such as monitor 110 described in FIGS. 1A and 1B. Optionally the evaluation process may be facilitated with controllable delivery of a stimulus using a stimulation evoking device 104, as described in FIG. 1A.

In stage 200, at least one physiological signal of a subject is acquired using at least one sensor.

In stage 204, the at least one physiological signal is analyzed and processed to extract at least two physiological parameters which are further classified using classifier algorithms.

In stage 206, an efficacy of SCS treatment is predicted and/or assessed based on the classified extracted physiological parameters. Optionally the results may be communicated to a user or device using communication modules, such as communication module 118 or via interface 120, as essentially described in FIGS. 1A and B. It is understood to one of ordinary skill in the art that the results may be presented in various forms, such as but not limited to, score, percentile, probability or the like.

Optionally, an additional stage 202, including providing at least one stimulus (pain evoking or non-pain evoking) to the patient may be included, as essentially described herein. The subject's reaction to a controlled and repeatable stimulation (in areas that are susceptible to pain as well as areas that are non-susceptible to pain) may further allow efficacy evaluation of SCS treatment for the subject being monitored.

Figure 2B:
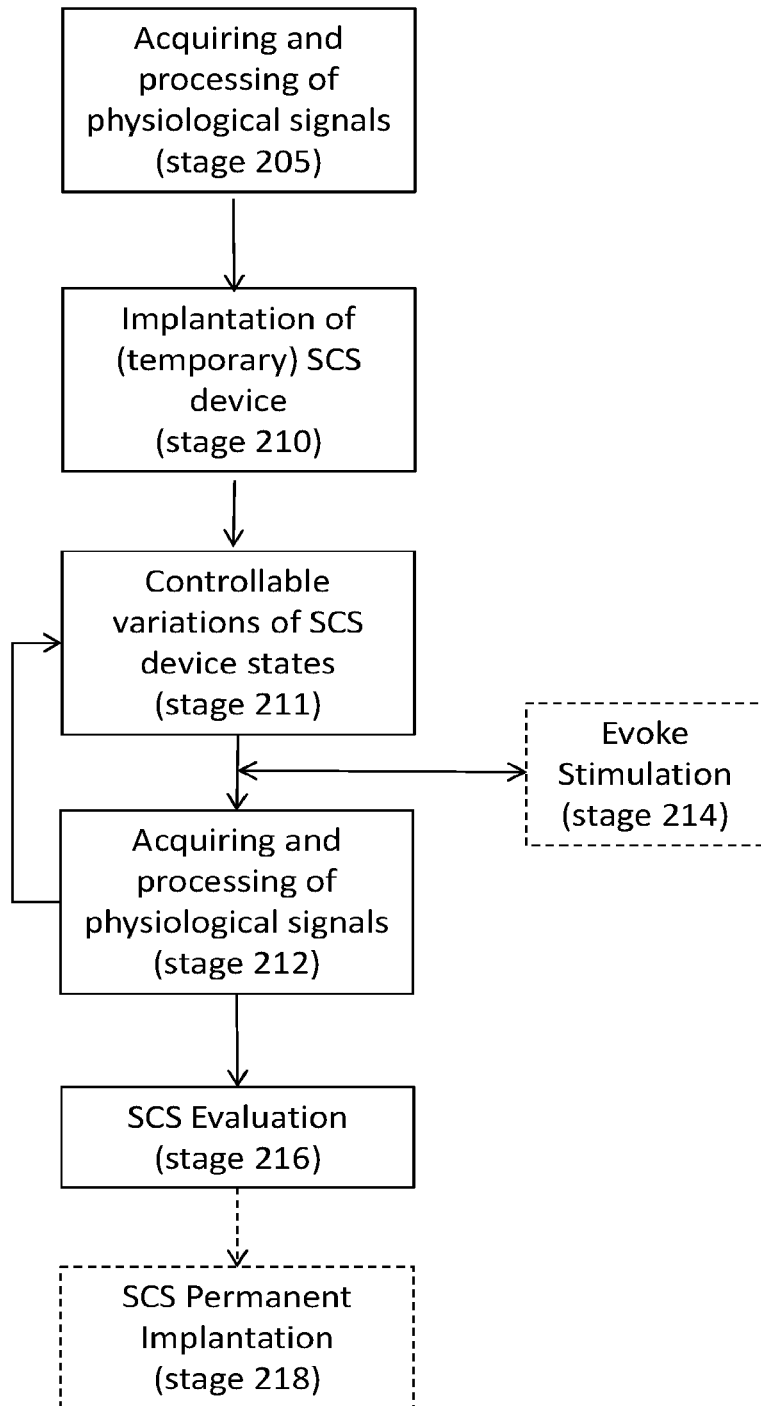
FIG. 2B is a flowchart of an exemplary method according to some embodiment.

Reference is now made to FIG. 2B which shows a flowchart of an exemplary method for evaluating SCS efficacy, according to some embodiments.

The method depicted in FIG. 2B is similar to that depicted in FIG. 2A, with the additional stage of placement of a temporary and/or permanent SCS device.

In stage 205 at least one physiological signal is acquired and processed to extract at least two physiological parameters which may be further classified using classifying algorithms. According to some embodiments, the processed and classified parameters may be indicative of a physiological status of the subject.

In stage 210 an SCS device, such as SCS device 102, described in FIG. 1B are associated with an individual.

In stage 211, the SCS device settings are controllably adjusted in order to provide an evaluation of SCS treatment for the individual. Preferably the stimulation provided by SCS device may be controlled at various levels for example ON/OFF states and/or settings of SCS parameters.

In stage 212 at least one physiological signal is acquired and processed to extract at least two physiological parameters which may be further classified using classifying algorithms. According to some embodiments, the processed and classified parameters may be indicative of an obtained SCS efficacy and/or of a physiological status of the subject. The at least one physiological signal may be acquired and processed for each of an ON and OFF state of the SCS device. For example, the at least one physiological signal may be initially acquired and processed when the SCS device is in its ON state and subsequently acquired and processed when the SCS device is in its OFF state.

Similarly, the at least one physiological signal may be acquired and processed for different SCS parameter settings. For example, looping between stages 212 and 211, as shown with arrow 209 may enable to gradually monitor a plurality of SCS parameters, in order to determine optimal settings for the SCS device.

Optionally in a stage 214 of providing at least one stimulus (pain evoking or non-pain evoking) to the subject may be included, as essentially described herein. The subject's reaction to a controlled and repeatable stimulation (in areas that are susceptible to pain as well as areas that are non-susceptible to pain) may further allow evaluation of SCS treatment efficacy in alleviating chronic pain.

In stage 216, an evaluation and scoring of the SCS treatment based on the classification of the physiological parameters that were acquired, processing as described in stages 205 and 212.

Optionally, if efficacy of a temporary SCS is evaluated, stage 218, may include implantation of a permanent SCS device, assuming positive results for the evaluation of the temporary SCS device.

Figure 3:
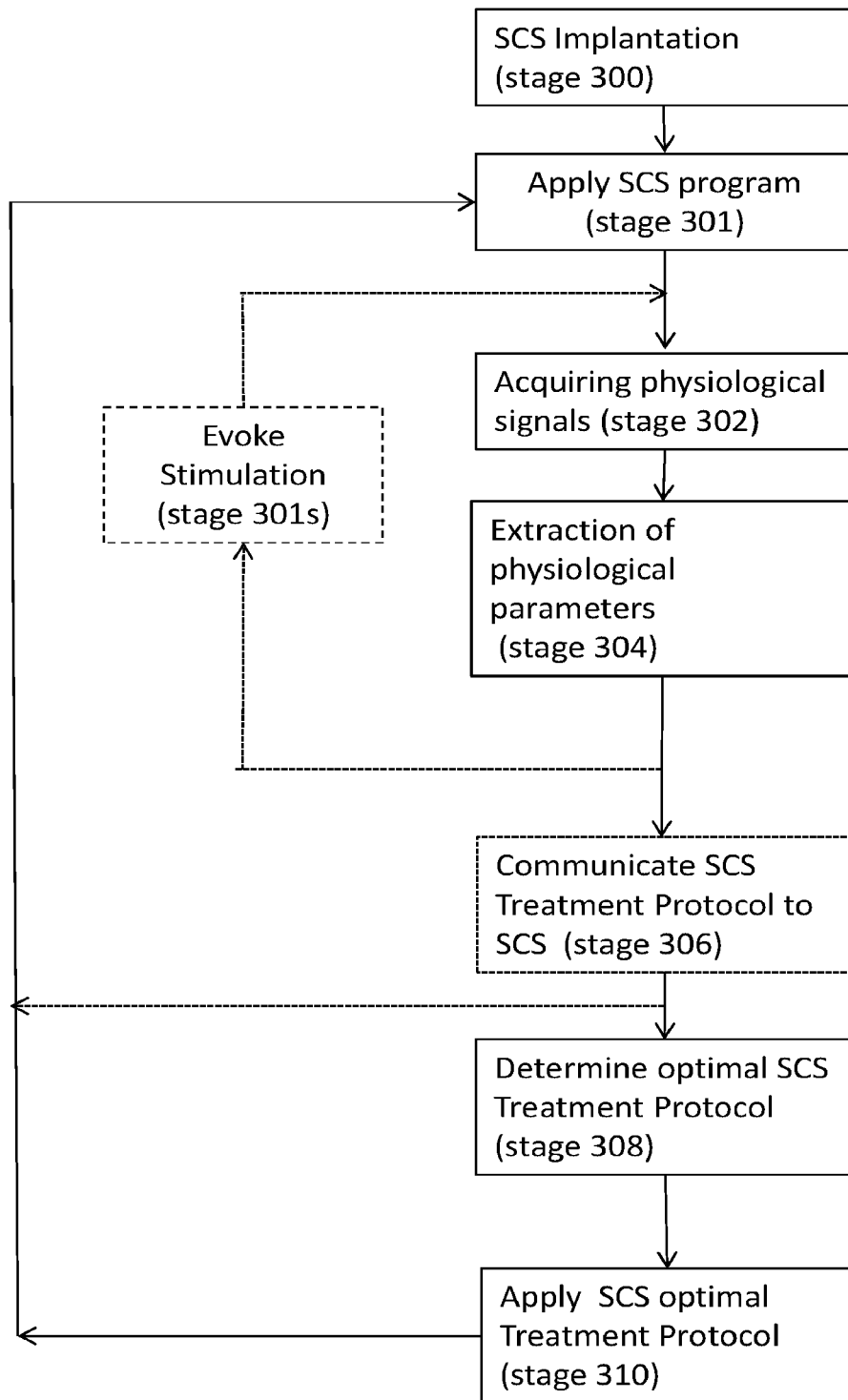
FIG. 3 is a flowchart showing an exemplary method according to some embodiment.

Reference is now made to FIG. 3 which depicts a flowchart showing a closed loop method for controlling an SCS device. The closed loop method may be utilized to ensure that an optimal SCS treatment protocol is implemented.

In stage 300 a SCS device is implanted in a subject suffering from chronic pain, and a monitoring device configured to monitor at least one physiological signal, such as monitor 110, is also associated with the user.

In stage 301, the SCS is configured to a certain SCS treatment program that is controlled and can be adjusted.

In stage 302, at least one physiological signal is acquired.

In stage 304 the at least one physiological signal is processed to extract at least two physiological parameters which may be further classified using classifying algorithms.

Optionally an additional stage 301*s* may be included. Stage 301*s* includes providing at least one stimulus (pain evoking or non-pain evoking) to the subject and subsequently evaluating the at least one physiological signal in response to the controlled and repeatable stimulation (in areas that are susceptible to pain as well as areas that are non-susceptible to pain), by the methods described herein.

Optionally, in stage 306, a treatment protocol is communicated to the SCS if the SCS is not already programmed or to the interface if manual program is required, and to optionally the evoked stimulation, optionally both using a wireless communication link.

In stage 308, an optimal SCS treatment protocol is determined based on the processed and classified parameters extracted from the physiological signals obtained in stages 302 and 304 as a result of changing stimulation in 301 and 301*s*, as essentially described herein.

In stage 310, the SCS device may receive, evaluate and implement the optimized SCS parameters and protocols, communicated in stage 308. The method may now revert to stage 301 for multistage programing.

Figure 4:
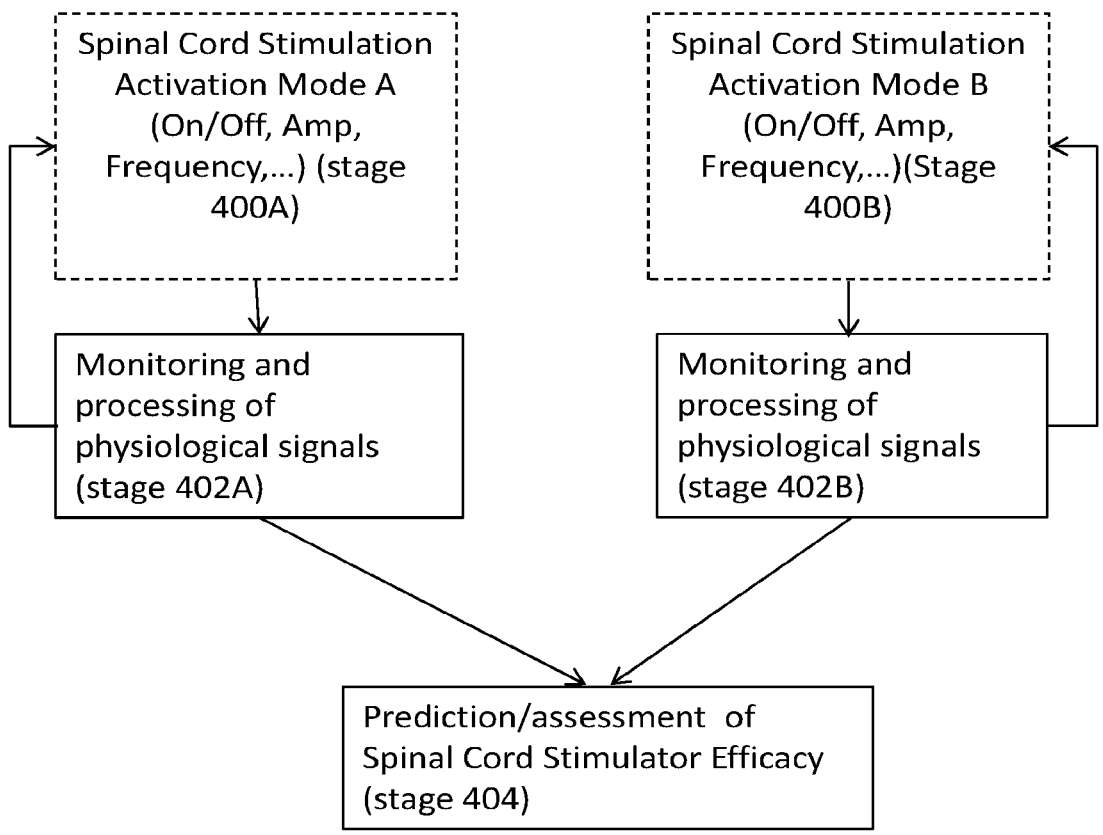
FIG. 4 is a flowchart showing an exemplary method according to some embodiment.

Reference is now made to FIG. 4 which shows a flowchart of an optional method for detecting and/or evaluating the efficacy of SCS treatment.

In stage 400A a SCS device is set at a first activation mode, referred to as activation mode A, for example SCS device is turned ON.

In stage 402A monitoring device, such as monitoring device 110, is provided and at least one physiological signal is acquired. The at least one physiological signal is processed to extract at least two physiological parameters which are further analyzed using a classifier algorithm to allow classification of a physiological status and/or SCS efficacy of the subject when the SCS device is in activation mode A, for example ON.

In stage 400B the SCS device is set at a second activation mode, referred to as activation mode B, for example SCS device is turned OFF.

In stage 402B the at least one physiological signal is acquired and processed to extract at least two physiological parameters which are further analyzed using the classifier algorithm to allow classification of a physiological status and/or SCS efficacy of the subject when the SCS device is in activation mode B, for example OFF.

Optionally activation mode A and B are alternate forms of the same stimulation parameter or device states. For example, if activation mode A is the ON state then activation mode B is the device OFF state. Additionally or alternatively, the activation modes A and B may refer to different values of a SCS parameter, such as but not limited to SCS frequency. Optionally a loop between stages 400A, 402A, 400B and 402B may be used such that all (or some) optional combinations of treatment parameters and protocols may be analyzed.

In stage 404 based on the monitoring results provided in stages 400A/B, 402A/B, a predication and/or evaluation of the SCS treatment efficacy may be provided.

EXAMPLES

Example 1: Radicular Pain 33 patients with chronic radicular (neuropathic) pain in one lower extremity and an implanted permanent spinal cord stimulator (SCS) participated in the study.

Patients were tested twice in a random order: first for 30 minutes after turning the SCS ON, and two hours after turning it OFF.

Patients were requested to rate the intensity of their radicular pain on numerical pain scale (NPS, 0-100) twice, at a random order: thirty minutes after turning the SCS on and two hours after turning it off. For the purpose of this study, a difference of 15 NPS points or more between the two ratings (stimulator "on" and "off") was regarded as an "effective SCS".

Plethysmogram (PPG) and Galvanic Skin Response (GSR) through the skin conductance were acquired for 120 seconds, using a monitoring device [PMD-100™ (Medasense, Israel)], to extract the following autonomic parameters: PPG amplitude, PPG amplitude variation, pulse rate (PR) interval, PR variability and GSR fluctuations.

The parameters were combined using a non-linear classifier. The accuracy, sensitivity, specificity, positive and negative predicted values (PPV and NPV) of each parameter alone and their combination were calculated. Paired t-test was used for statistical analyses.

Results: Effective SCS was found in 18 patients and ineffective in 15 patients (ΔNPS: 40±17 vs. 8.5±7, respectively; $p<0.05$). The combination of the parameters outperformed each of the parameters alone in the detection of the SCS effectiveness, with regards to all classification performance criteria (accuracy of the combination was 85% and that of each parameter ranged from 52% to 70%; sensitivity 94% vs 53-82%; specificity 75% vs 38-73%; PPV 76% vs 64-76%; NPV 92% vs 46-79%).

Conclusions: This shows that autonomic-based multi-parameter assessment provided by the monitor disclosed herein may be used for objective measurement of SCS effectiveness.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. Unless otherwise defined, all technical and scientific terms used herein have the same meaning as commonly understood by one of ordinary skill in the art to which this invention belongs.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A system for calibrating spinal cord stimulation (SCS) treatment in a subject, the system comprising a processing module, a sensor module and a classifier module; wherein the processing module is configured to:
receive a first indication from a SCS device that a first SCS treatment is being provided;
wherein the first SCS treatment is characterized by a first value of at least one SCS parameter,
wherein the first value of the at least one SCS parameter is different from that of a second value of the at least one SCS parameter;
initiate the sensor module to conduct a first measurement of at least one physiological signal in response to the first indication from the SCS device;
wherein the at least one physiological signal comprises at least one of a PPG signal or movement (accelerometer) signal;
receive a second indication from the SCS device that a second SCS treatment is being provided; wherein the second SCS treatment is characterized by the second value of the at least one SCS parameter;
initiate the sensor module to conduct a second measurement of the at least one physiological signal in response to the second indication from the SCS device;
initiate the classifier module to, by a non-transitory computer program, extract at least two features from each of the at least one physiological signal obtained from the first and second measurements;
wherein the at least two features comprise PPG amplitude, PPG amplitude variation, pulse rate (PR) interval, PR variability, 3-axis accelerometer data (X, Y, Z, Theta) value, 3-axis accelerometer data (X, Y, Z, Theta (θ)) average value, 3-axis accelerometer data (X, Y, Z, Theta (θ)) variability or any combination thereof;
classify the at least two features by applying a classification algorithm thereon; and output,
based on the classification, whether the first SCS treatment or the second SCS treatment correlates with a higher efficacy.

2. The system according to claim 1, wherein the processing module is further configured to select a value of the one SCS parameter yielding a highest efficacy based on the classification.

3. The system according to claim 1, wherein varying the SCS parameters comprises changing the SCS parameter over its dynamic range and making at least one of continuous, incremental or step wise changes in the value of the SCS parameter.

4. The system of claim 1, wherein the remaining of the at least one SCS parameters are fixed while varying the one SCS parameter.

5. The system of claim 1, wherein the at least one SCS parameter comprises a type of stimulation, stimulation frequency, duration, pulse width, intensity, waveform, wave pattern, signal, amplitude, onset timing, delay, treatment length, treatment period, onset delay, or any combination thereof.

6. The system of claim 1, wherein applying the classification algorithm further comprises directly or indirectly comparing the first and second measurements to pre-stored data sets of measurements obtained from subjects with known SCS treatment efficacies and taking into consideration demographic data of the patient.

7. The system of claim 1, further comprising a SCS device.

8. The system of claim 1, wherein the at least two features further comprise photoplethysmograph (PPG) Peak (P) amplitude, mean PPG Peak (P) amplitude, standard deviation (std) of PPG Peak (P) amplitude, Trough (T) amplitude, mean Trough (T) amplitude, std of Trough (T) amplitude; PPG dicrotic notch (N) amplitude, mean dicrotic notch (N) amplitude, std of dicrotic notch (N) amplitude, PPG peak to peak time intervals, PPG peak to peak interval mean, PPG peak to peak interval std; power spectrum of the PPG peak to peak intervals: VLF Power, LF Power and HF Power; galvanic skin response (GSR) amplitude, GSR mean amplitude, GSR amplitude std; GSR Peak (P) amplitude, mean Peak (P) amplitude and Peak (P) amplitude std; GSR peak to peak time intervals, mean GSR peak to peak time interval; GSR peak to peak time intervals std; Phasic EDA: amplitude, mean amplitude and std of amplitude, Temperature amplitude, mean amplitude and std of amplitude; Temp Peak (P) amplitude, mean amplitude and std of amplitude; Temperature peak to peak time intervals, mean and std (variability) of interval; ECG to PPG Pulse Transition time; PPG to PPG Pulse Transition time; ECG R to R time intervals, mean and std (variability) of intervals; Power of VLF, LF and HF frequency bands of power spectrum of the ECG R to R intervals (heart rate variability); Upper peak amplitude, mean amplitude and STD of amplitude; Respiratory rate, mean rate and std rate; Power of the frequency bands of power spectrum of EMG signal; EMG Power Spectrum Mean frequency; EMG Power Spectrum Highest Peak Frequency; Power of the alpha, beta, gamma, delta, theta frequency bands of power spectrum of EEG/FEMG signal; EMG Power Spectrum Mean frequency; EMG Power Spectral edge frequency; Coherence between 2 or more EEG/FEMG channels; frequency of movement; axis of movement; or any combination thereof.

9. The system of claim 1, wherein the at least one physiological signal further comprises an electrocardiogram (ECG) signal, a blood pressure signal, a respiration signal, an internal body temperature signal, a skin temperature signal, a electrooculography (EOG) signal, a pupil diameter signal, a electroencephalogram (EEG) signal, a frontalis electromyogram (FEMG) signal, a electromyography (EMG) signal, an electro-gastro-gram (EGG) signal, a laser Doppler velocimetry (LDV) signal, a dynamic light scattering (DLS) signal, a near-infrared spectroscopy (NIRS) signal, a partial pressure of carbon dioxide signal, or an accelerometer reading.

10. The system of claim 1, wherein the processing module is further configured to display a first efficacy of the first SCS treatment and a second efficacy of the second SCS treatment.

* * * * *